United States Patent [19]

Corbitt, Jr. et al.

[11] Patent Number: 5,082,111
[45] Date of Patent: Jan. 21, 1992

[54] SURGICAL INSTRUMENT HOLDER

[75] Inventors: John D. Corbitt, Jr.; Kenneth M. Kuzmick, both of West Palm Beach; Stephanie L. O'Hearn, Boca Raton, all of Fla.; Albert N. Santilli, Gates Mills, Ohio

[73] Assignee: Surgical Concepts, Inc., Cleveland, Ohio

[21] Appl. No.: 667,964

[22] Filed: Mar. 12, 1991

[51] Int. Cl.5 .................. B65D 73/00; A61M 25/02
[52] U.S. Cl. ........................ 206/363; 128/DIG. 15; 206/478; 211/70.6; 248/205.3
[58] Field of Search ............ 206/362, 362.1, 363-379, 206/438, 460, 477-482; 211/13, 70.6, 86, 88; 248/205.3, 309.1, 316.5; 128/DIG. 15, DIG. 26

[56] References Cited

U.S. PATENT DOCUMENTS

| | | | |
|---|---|---|---|
| 3,696,920 | 10/1972 | Lahay | 206/370 |
| 4,074,397 | 2/1978 | Rosin | 128/DIG. 15 |
| 4,210,244 | 7/1980 | Westrick | 206/370 |
| 4,665,566 | 5/1987 | Garrow | 128/DIG. 15 |
| 4,738,662 | 4/1988 | Kalt et al. | 128/DIG. 15 |
| 4,793,483 | 12/1988 | Holmes | 206/363 |

Primary Examiner—Jimmy G. Foster
Attorney, Agent, or Firm—Weston Hurd Fallon Paisley & Howley

[57] ABSTRACT

A disposable surgical instrument holder for holding a number of surgical instruments, tubes and wires includes a narrow, elongate base member that can be attached adhesively to a patient's body or drape. A plurality of flaps are releasably attached to the base member by way of hinges and hook and loop fasteners. Each flap can be pulled back from the base member and then can be resecured once an instrument has been inserted between the flap and the base member. The holder can be provided with a sheet of abrasive material in order to permit surgical instruments to be cleaned during the course of an operation. The holders can be stored within sterile packages for use whenever convenient to the surgeon.

18 Claims, 3 Drawing Sheets

SURGICAL INSTRUMENT HOLDER

BACKGROUND OF THE INVENTION

1. Field of the Invention

The invention relates to techniques for securing surgical instruments and equipment during surgery and, more particularly, to techniques for securing surgical instruments and equipment close to the surgical area.

2. Description of the Prior Art

Surgical procedures require the use of various types of instruments and equipment. As used herein, the term "instruments" or "surgical instruments" will refer to all types of surgical instruments and equipment, including scalpels, scissors, suction tubes, cauterizers, and so forth. It is necessary that the instruments be available close to the surgical site. Desirably, the instruments would be attached to the patient's body, or to drapes or covers shielding the patient's body, in order to minimize inconvenience to the surgeon. Unfortunately, due to the uneven surfaces afforded by the patient's body, it has been impractical for instruments to be located any closer than a nearby surgical tray.

An early approach to the problem with respect to tubes and wires was the use of various clamps which surrounded the patient's head or a limb. The tube or wire to be clamped then was held in a stable position between the clamp and a body part. Although the referenced approach resulted in the immobilization of the tube or wire, it was not useful for the securing of surgical instruments which might require repeated removals and reinsertions into the holding device. Further, such clamps were difficult to use with a plurality of tubes and wires which needed to be segregated from one another.

Another approach to the problem has been to use two separable pieces of material and then to clamp the instrument between the two pieces of material, as disclosed by Kalt et al. in U.S. Pat. No. 4,738,662, issued Apr. 19, 1988. One piece of material is attached to a body part, the instrument is placed on the attached material, and then the second piece of material clamps the instrument in place by adhering the second piece of material to the first piece of material.

Certain problems exist with the device disclosed in the Kalt patent. Since two individual pieces of material are used to hold the instruments, difficulties may arise in keeping track of the piece which is not attached to the body. This is especially true if several of the devices are to be used in series, such as on an arm or a leg. Further, as with the previously discussed clamps, the Kalt device itself is designed as a clamp. As such, its purpose is to lock the instrument that it is holding into an immobile position. Such a device is ineffective for use as a holder, where instruments may have to be removed and reinserted into the holder several times during a single operation. The Kalt patent would require disengaging the releasable flap, repositioning the instrument, then resecuring the instrument. Such a process would be no more useful than using a conventional surgical tray.

U.S Pat. No. 4,074,397, issued Feb. 21, 1978 to Rosin, discloses a disposable pad for securing cords, tubes and the like. Rosin's device consists of a relatively large, square, flexible pad having an adhesive side that may be attached to a convenient supporting surface such as a surgical drape. The pad has an elongate strip attached to, or integral with, the pad. The strip has a hook and loop fastener affixed to its distal end. By wrapping the strip around the tube to be secured and then pressing the hook and loop fastener onto the pad itself, the tube is secured. Tubes also may be shifted back and forth within the wrapped strip.

Despite the advances made by the Rosin patent, certain problems have not been addressed. Although the pad permits a broader range of attachment locations for tubes to be used, the size and shape of the pad is restrictive. Areas on a patient's body or drape that are not amenable to the use of a large, square pad cannot be used as a site for the attachment of instruments. Furthermore, the singularity of the pad is restrictive, that is, a single pad can be used to hold only a single instrument. During surgery, a number of instruments often are needed to be kept at hand. Although several pads might be used simultaneously, such an arrangement soon would use up available attachment areas on the patient's body or drape. Also, the use of many large pads would clutter up the surgical area.

U.S. Pat. No. 4,665,566 issued May 19, 1987 to Garrow discloses a strap-like clamping device. Although Garrow shows the use of a multiplicity of tube-holding flaps, the device is limited to use in only certain areas. This is because the strap can be attached only to objects, such as a patient's head, that the strap can be passed around. The device thus limits itself to uses where an extremity is available.

Desirably, a surgical instrument holder would be relatively small and would have the capacity for holding a number of surgical instruments while being able to be attached anywhere on a patient's body or drape. Further, such a holder would be presterilized and disposable in order to eliminate the necessity of repeated sterilization.

SUMMARY OF THE INVENTION

In response to the foregoing concerns, the present invention provides a new and improved surgical instrument holder. The holder according to the invention can hold a number of surgical instruments simultaneously. Further, it is usable in areas that normally cannot accommodate other instrument holders.

The holder according to the invention comprises a narrow, elongate base member that can be attached adhesively to a patient's body or drape. A plurality of flaps are attached releasably to the 10 base member. Each flap can be pulled back from the base member and then can be resecured once an instrument has been inserted between the flap and the base member. This means of securing the instrument not only keeps it secured in one place, but it also permits other instruments to be retained separately by the holder.

In the preferred embodiment, the holder comprises a base member to which a plurality of flaps are releasably attached by means of hook and loop fasteners on the contacting surfaces of the flaps and base member. Each flap comprises a tab portion, a body portion and a hinge portion. The hinge portion permanently attaches the flap to the base member. The hinge preferably is in the form of an ultrasonic weld.

A feature of the invention relates to the material used on the contacting surfaces of the base member and the flaps. The material used is Velcro ® or a similar hook and loop material that will conform to the shape of any instrument placed between the contacting surfaces. In effect, the flap and base member define a receptacle within which the instrument can be retained. This feature permits an instrument to be repeatedly removed and reinserted into the holder without having to reattach the flap each time. Thus, once an instrument initially is placed in the holder, each flap customizes itself to the shape of each instrument.

A further feature of the invention is a two-sided elongate base member. One side of the base member comprises a hook or loop tape, while the other side of the base member includes an adhesive surface that is covered by a removable, protective sheet. After removing the protective sheet, the holder may be attached to exposed portions of the patient's body or to exposed surfaces of sterile surgical drapes wherever convenient to the surgeon.

The holders according to the present invention are disposable. Accordingly, they can be removed along with the surgical drapes to which they are attached. This reduces clutter around the surgical theater. Furthermore, the preferred holders can be dispensed as multi-flap, sterile packages; the surgeon can hold any number of instruments by utilizing as many packages as are needed without contaminating the remaining packages.

Another feature of the invention is the incorporation of a fluorescent dye into exposed surfaces of the flaps. The fluorescent dye permits surgeons to find instruments easily during surgery. In addition, the contrast provided by the dye permits instruments to be found more easily at the end of surgery. This decreases the chance of accidentally misplacing an instrument, either in the surgical theater or within the patient's body.

In an alternative embodiment of the invention, a sheet of abrasive material projects from one end of the base member. The remaining portions of the base member still may be used for the attachment of surgical instruments. The use of a sheet of abrasive material is especially helpful to surgeons using suction tubing or other instruments that tend to become coated or clogged with body tissue (debris) during surgery. Rather than having to interrupt the surgical procedure and either replace the coated or clogged instruments, or clean the instruments at a distance from the surgical field, the surgeon simply can use the abrasive material included as part of the surgical holder to clean the instruments.

The foregoing and other features and advantages of the invention are illustrated in the accompanying drawings and are described in more detail in the specification and claims that follow.

DESCRIPTION OF THE PREFERRED EMBODIMENT

Figure 1:
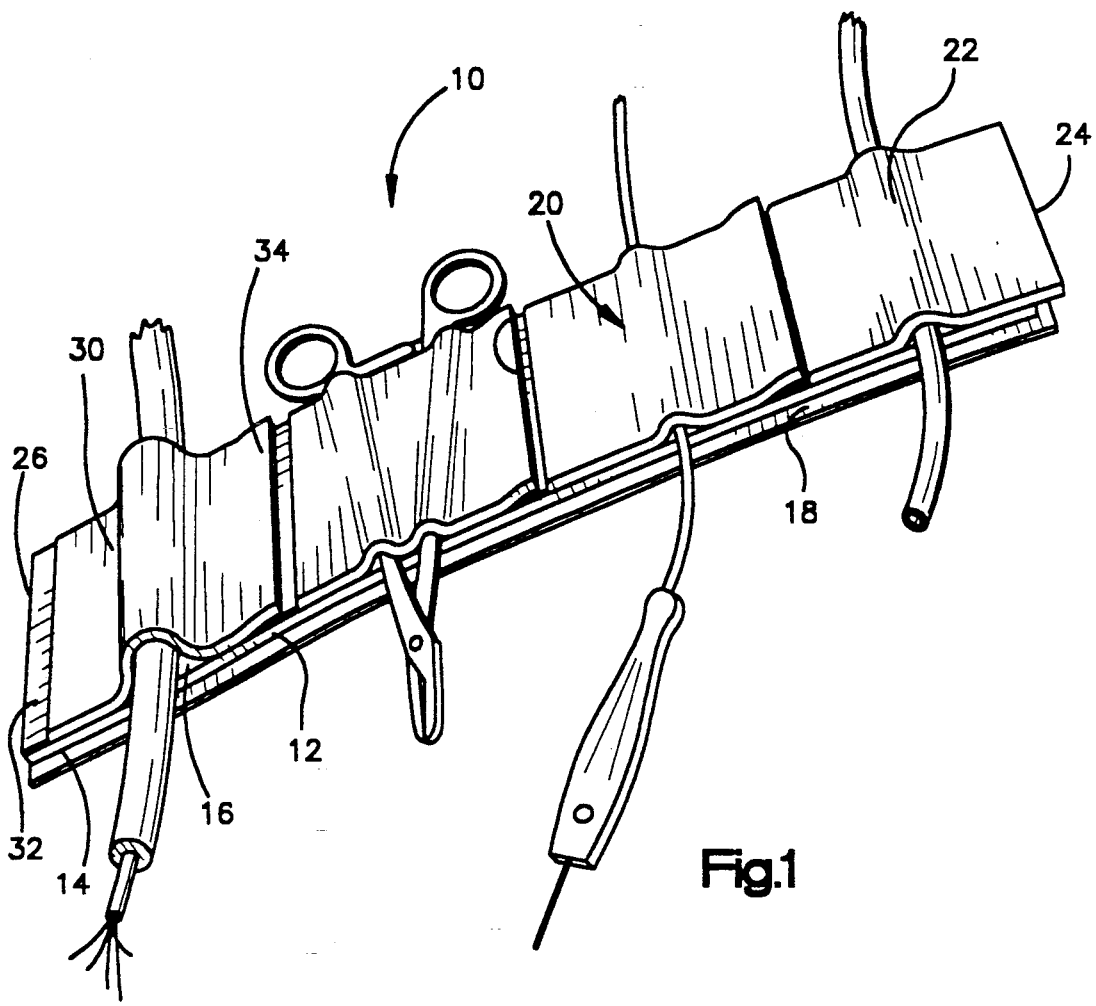
FIG. 1 is a perspective view of a surgical instrument holder according to the invention showing instruments as they might be secured in place during surgery.

During a typical surgical procedure, disposable drapes cover those portions of the patient's body that are not involved directly in the surgical procedure. Once the patient has been draped and the surgical site on the patient has been exposed, the physician uses a variety of instruments to incise, scrape, irrigate and clamp various body tissues. The surgical instruments frequently are moved back and forth between a surgical tray nearby the patient and the surgical site that is being addressed. The current invention relates to a disposable surgical instrument holder that may be attached to either the drape or the patient, usually in the region of the surgical site.

Referring to FIGS. 1-5, a surgical instrument holder according to the invention is indicated generally by the reference numeral 10. The holder 10 includes an elongate base member 12 in the form of a flexible sheet of polymeric material. The base member 12 has a first surface 14 and an opposed, second surface 16. The first surface 14 includes an adhesive layer, while the second surface 16 includes a plurality of upstanding hooks. A protective sheet 18 is disposed over the adhesive surface 14. The base member in the preferred embodiment is about 10 inches long by 2 inches wide.

A plurality of flaps 20 in the form of flexible sheets of polymeric material are secured to the base member 12. The flaps 20 are arranged end-to-end so as to form an elongate strip of flaps 20. Each of the flaps 20 includes a body portion 22, which body portion 22 includes a first end 24 and a second end 26. The body portion 22 also includes a first surface 28 and an opposed, second surface 30. The first surface 28 includes a plurality of loops that interact with the hooks included as part of the second surface 16. If desired, the second surface 30 can be colored with a fluorescent dye in order to increase the visibility of the holder 10. A hinge 32 in the form of an ultrasonic weld defines the second end 26 and secures it to the base member 12. A tab 34 extends from the body portion 22 and defines the second end 26. Each flap 20 preferably is about 2½ inches in length.

Figure 2:
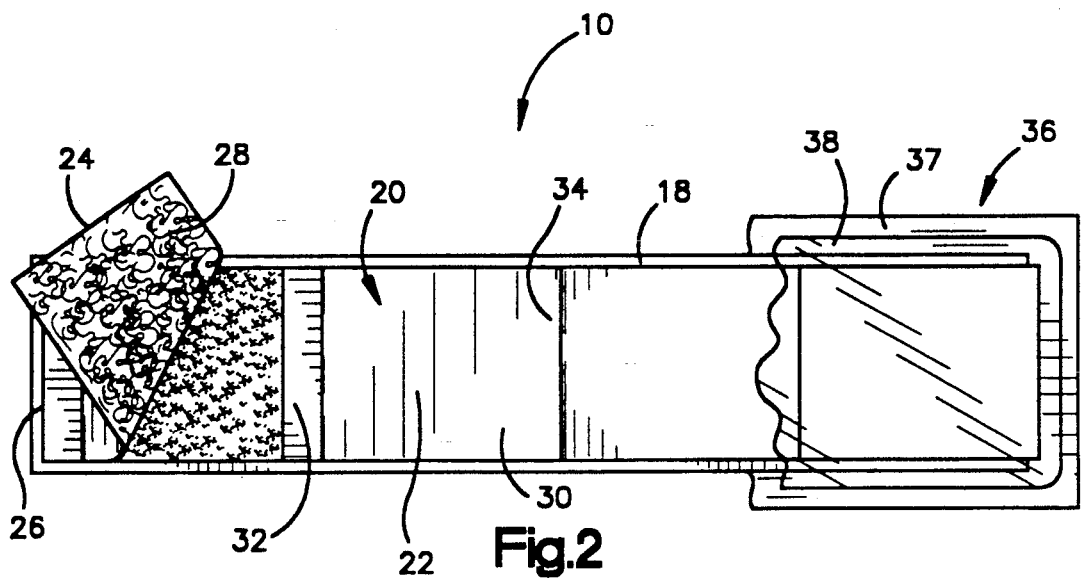
FIG. 2 is a top plan view of the surgical instrument holder of FIG. 1 with the instruments removed.
Figure 3:
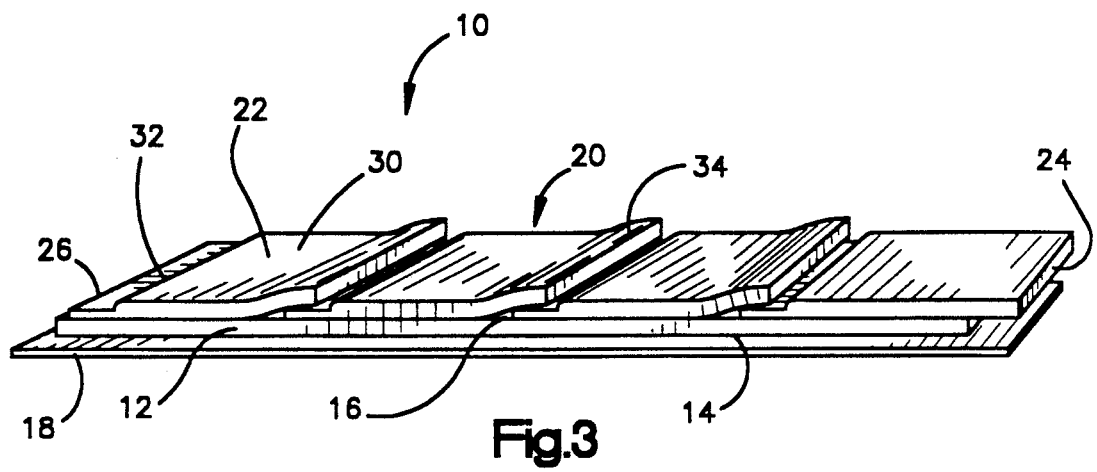
FIG. 3 is a perspective view of the surgical instrument holder of FIG. 2 with instrument-holding flaps in a closed position.
Figure 4:
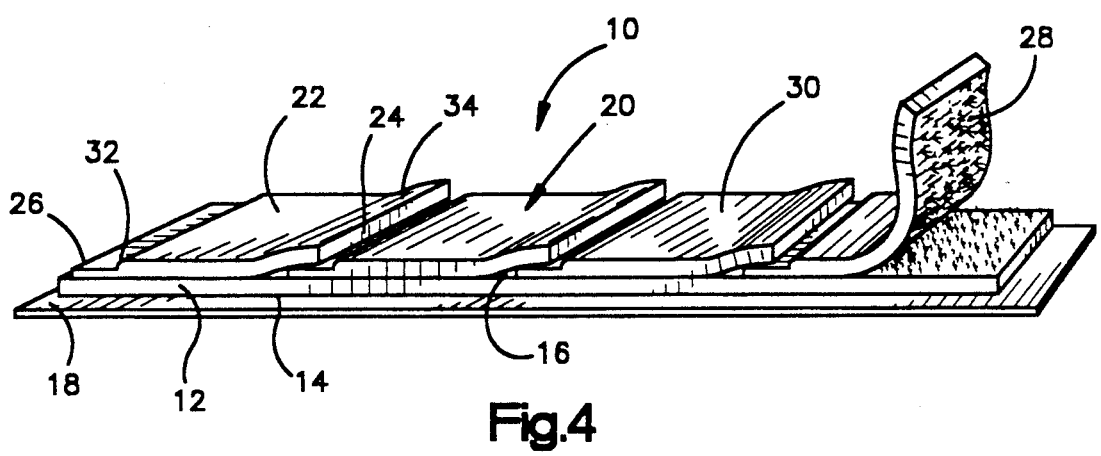
FIG. 4 is a view similar to FIG. 3, showing one flap in an open position.
Figure 5:
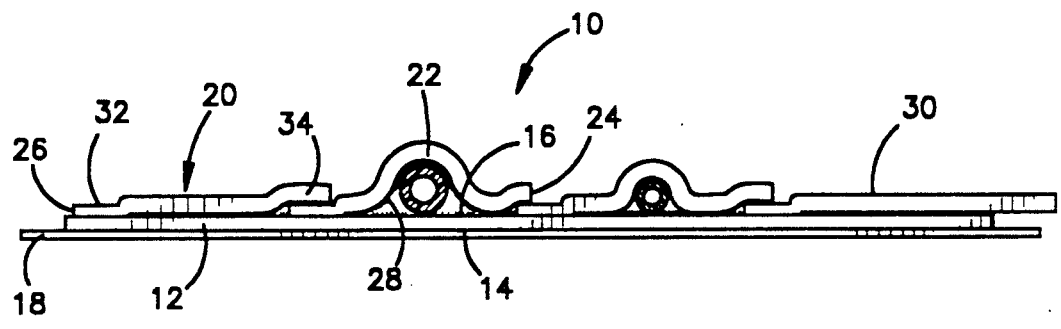
FIG. 5 is a side elevational view of the surgical holder instrument of FIG. 1 as it might be used to hold tubular instruments of various sizes.

The holder 10 is disposed within a package 36 (FIG. 2). The package 36 includes a layer 37 of Tyvek ™ or similar non-tearable paper to which a sheet 38 of a transparent plastics material is secured at the edges. The layer 37 and the sheet 38 form an airtight pouch that maintains the holder 10 in a sterile condition. The holder 10 can be sterilized within the package 36 by conventional techniques such as gas sterilization or gamma ray sterilization. Reference is made to U.S. Pat. No. 4,367,816, for a disclosure of a suitable sterilizable package that can be used for the holder 10. As will be apparent, the package 36 can be used to hold the alternative embodiments of the invention that are described hereinafter.

Figure 6:
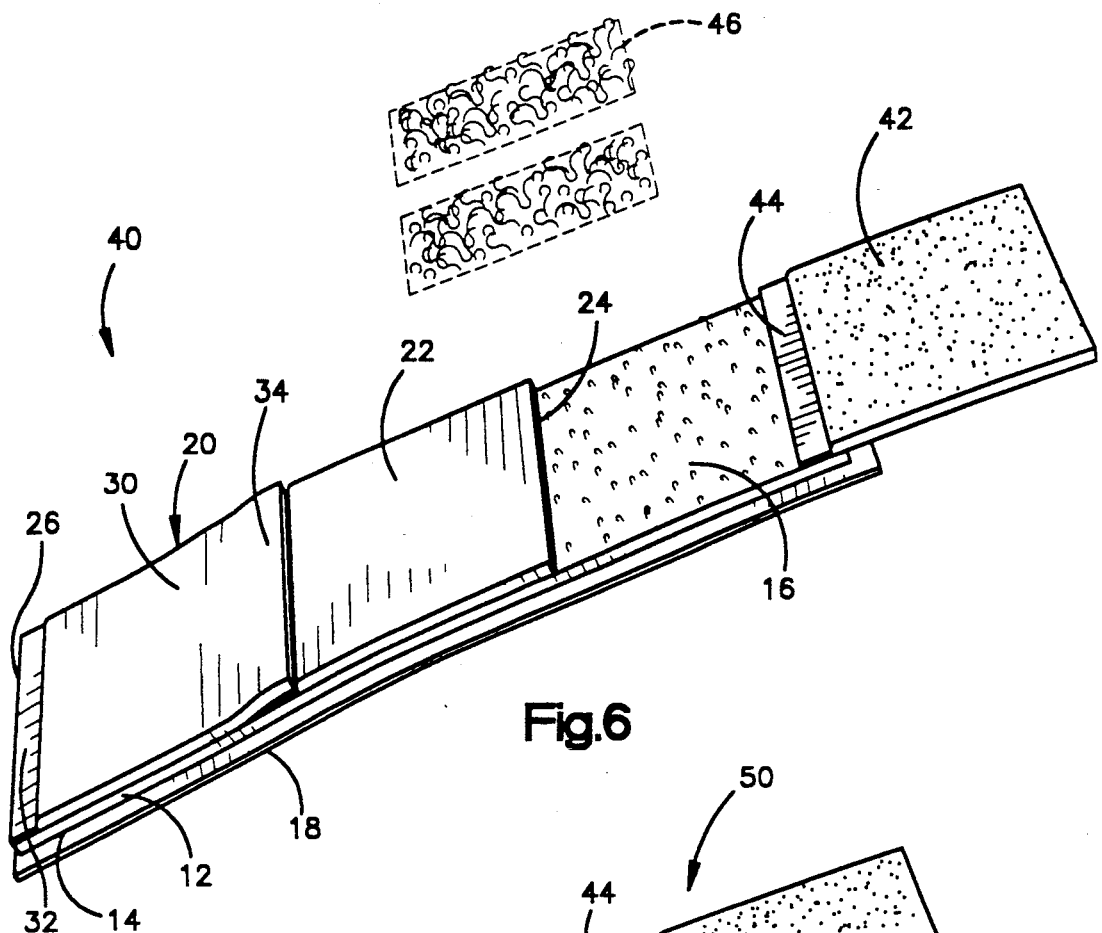
FIG. 6 is a perspective view of an alternative embodiment of the surgical instrument holder according to the invention with a sheet of abrasive material attached to one end.

Referring now to FIG. 6, an alternative embodiment of the surgical instrument holder according to the invention is indicated generally by the reference numeral 40. Because many of the elements employed as part of the holder 40 are the same as those employed as part of the holder 10, like reference numerals will be used where appropriate. In the holder 40, one of the flaps 20 (to the right as viewed in FIG. 6) has been removed. A sheet of abrasive material 42 has been secured to the end of the base member 12 by means of an ultrasonic weld 44. The abrasive material 42 is available from 3-M Corporation as Safety-Walk general purpose abrasive, medium grade, in two-inch wide rolls. The abrasive material 42 is in the form of a polymeric sheet having a layer of adhesive on one surface. The adhesive layer is protected by a removable protective sheet 46. The abrasive material extends the overall length of the surgical instrument holder by about 2 inches, making the holder 40 about 12 inches long.

A pair of small flaps 46, each about half the width of the flaps 20, also are included as part of the holder 40. The flaps 46 are made of the same material as the flaps 20. Accordingly, the flaps 46 can be used to secure instruments to the base member 12 in that region of the base member 12 adjacent the sheet of abrasive material 42. Each flap preferably is about 2½ inches in length and ⅜ inch wide.

Figure 7:
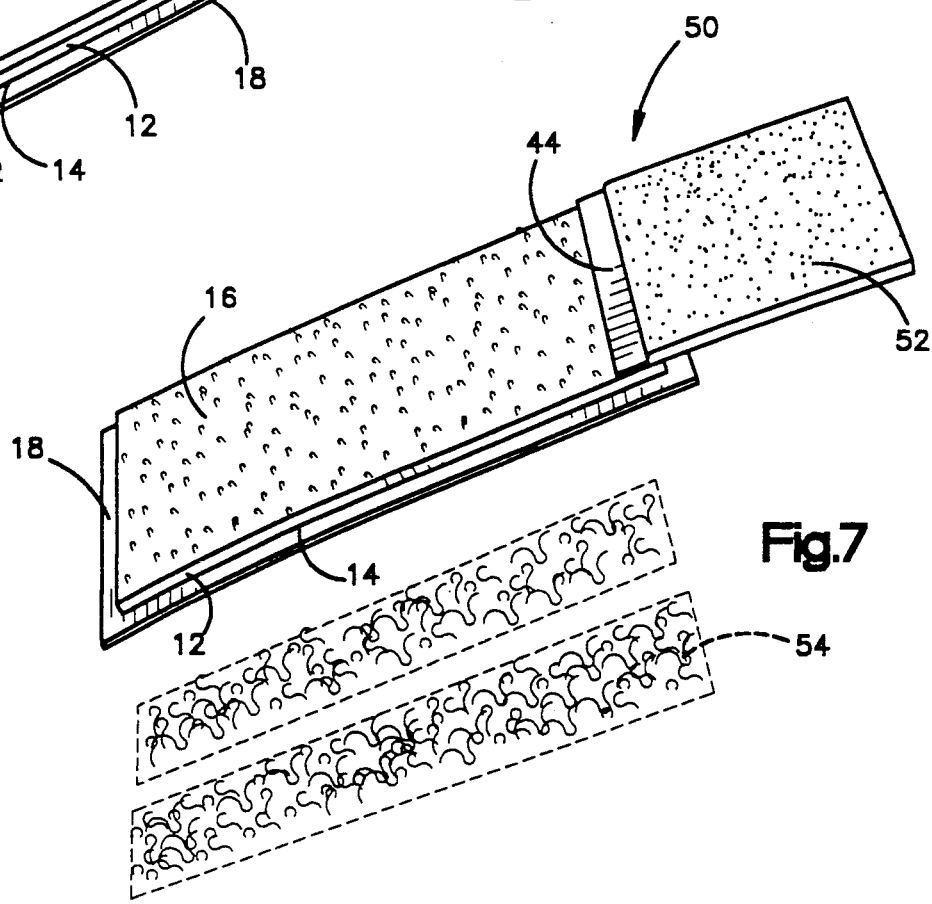
FIG. 7 is a view similar to FIG. 6, showing an exposed contacting surface of a base member with a sheet of abrasive material attached to one end of the base member.

Referring now to FIG. 7, a second alternative embodiment of the surgical instrument holder according to the invention is indicated generally by the reference numeral 50. The holder 50, like the holder 40, employs certain of the elements that are employed with the holder 10 and, where appropriate, like reference numerals will be used. As with the holder 40, the holder 50 includes a sheet of abrasive material 52. Unlike the holders 10 and 40, the holder 50 does not include any flaps 20 that are permanently secured to the base member 12. Rather, the holder 50 includes a pair of small flaps 54 that are made of the same material as the flaps 20, but which are not connected to the base member 12. Accordingly, the flaps 54, like the flaps 46, can be applied to the second surface 16 wherever desired in order to secure instruments to the base member 12 in any desired location on the base member 12.

OPERATION

When the surgeon determines which of the surgical instrument holders 10, 40, 50 is required for a given surgical procedure, the surgeon selects one or more packages 36 containing the holders 10, 40, or 50. Thereafter, the holder 10, 40, or 50 can be removed from the package 36. The holder 10, 40, or 50 then can be attached to the surgical drape or a portion of the patient's body near the site of the operation. Attachment of the holder is accomplished by removing the protective sheet 18 from the base member 12 and contacting the adhesive surface 14 to the drape or the patient.

Once the holder 10 is in place, the surgeon can begin securing whatever instruments will be needed for the surgery. This is done by a series of simple steps. First, the surgeon grasps one of the tabs 34 and pulls the associated flap 20 away from the base member 12 to expose the second surface 16 of the base member 12. A surgical instrument then is placed on the exposed surface 16. Once the instrument has been placed on the surface 16, the flap 20 is closed over the instrument. This is accomplished by recontacting the portion of the exposed surface 16 of the base member 12 not covered by the instrument with the second surface 26 on the underside of the flap 20. Pressure is applied to the flap to engage the surfaces 16, 26.

Once the flap 20 is closed, the flap 20 forms a receptacle for whatever instrument that is disposed between the base member 12 and the flap 20. The surgeon can quickly and easily remove and reinsert instruments throughout the duration of the operation. If the holders 40, 50 have been selected, the abrasive material 32 can be used to clean surgical instruments during the course of the operation. Once the operation has been completed, the surgical instrument holders 10, 40, 50 can be disposed along with the surgical drapes.

The present invention provides a number of advantages as regards securing surgical instruments. Because the holders 10, 40, 50 are relatively short and narrow, they can be dispensed as part of individual, sterile packages that are separate from other packages without disturbing the sterility of the other packages. Accordingly, any desired number of holders 10, 40, 50 can be dispensed at a given time without disturbing the remaining, unused packages 36.

As will be apparent from the foregoing description, the holders according to the invention can be attached easily to a patient's body or surgical drape. Surgical instruments of a wide variety of sizes and shapes can be held easily merely by lifting one of the flaps, positioning the instrument, and reattaching the flap. The flap forms a receptacle that permits the instrument to be withdrawn and reinserted, without removing the flap, if desired. If the holders 40 or 50 have been selected, the abrasive material 32 will enable the surgeon to easily and quickly clean debris from the surgical instruments. Moreover, if the flaps 20 have been stained with a fluorescent dye, the instruments held by the holders 10, 40 or 50 can be found easily during surgery, and it will be less likely that any instruments will be lost or misplaced at the end of surgery. Because is it expected that the holders 10, 40, 50 will be inexpensive to manufacture, the holders 10, 40, 50 can be discarded at the end of the operation, together with the surgical drape and any other disposable equipment used during the operation.

Although the invention has been described in its preferred form with a certain degree of particularity, it will be understood that the present disclosure of the preferred embodiment has been made only by way of example and that various changes may be resorted to without departing from the true spirit and scope of the invention as hereinafter claimed. It is intended that the patent shall cover, by suitable expression in the appended claims, whatever features of patentable novelty exist in the invention disclosed.

What is claimed is:

1. A device for holding surgical instruments, comprising:
   a base member having first and second opposed surfaces, the first surface including an adhesive layer;
   a plurality of flaps connected to the base member, each flap including:
   a body portion having first and second ends, and
   a hinge connecting the first end of the body portion to the second surface of base member; and
   means for releasably connecting the body portion of each flap to the second surface of the base member.

2. The device of claim 1, wherein the hinge of a given flap is disposed proximate to the tab of an adjacent flap when the flaps are in contact with the base member.

3. The device of claim 2, wherein the flaps are arranged end-to-end so as to form an elongate strip of flaps.

4. The device of claim 1, wherein each flap includes a tab at the second end of the body portion.

5. The device of claim 1, further comprising a sterile package within which the device is disposed.

6. The device of claim 1, wherein the body portion of each flap comprises first and second opposed surfaces, the second surface being in contact with the second surface of the base member.

7. The device of claim 6, wherein the means for releasably connecting the body portion of each flap to the second surface of the base member includes hook material disposed on the second surface of each flap, the second surface of the base member loop material.

8. The device of claim 6, wherein the means for releasably connecting the body portion of each flap to the second surface of the base member includes loop material on the second surface of each flap, the second surface of the base member including hook material.

9. The device of claim 1, wherein the hinge comprises an ultrasonic weld.

10. The device of claim 1, wherein each flap is colored with a fluorescent dye.

11. The device of claim 1, further comprising a sheet of abrasive material connected to the base member and projecting from one side thereof.

12. The device of claim 11, wherein the abrasive material comprises a medium-grade textured scratch pad.

13. The device of claim 1, further comprising a layer of protective material disposed over the first surface of the base member, the layer of protective material being removable so as to expose the adhesive layer.

14. A device for holding surgical instruments, comprising:
an elongate base member having first and second opposed surfaces, the first surface including an adhesive layer;
a layer of protective material disposed over the first surface of the base member, the layer of protective material being removable so as to expose the adhesive layer;
a plurality of flaps connected to the base member and arranged end-to-end so as to form an elongate strip, each flap including:
a body portion having first and second ends and first and second opposed surfaces, the first surface being exposed to the user and the second surface being in contact with the second surface of the base member,
a hinge connecting the first end of the body portion to the second surface of the base member, and
a tab at the second end of the body portion, the tab projecting upwardly from the body portion of the flap so as to remain out of contact with the second surface of the base member, and
means for releasably connecting the second surface of each flap to the second surface of the base member, the means for releasably connecting including hook material included as part of a selected one of the second surface of the flaps or the base member, and loop material included as part of the other of the second surface of the flaps or the base member.

15. The device of claim 14, further comprising a sterile package within which the device is disposed.

16. The device of claim 14, wherein the hinge comprises an ultrasonic weld.

17. The device of claim 14, wherein the first surface of each flap is colored with a fluorescent dye.

18. The device of claim 14, further comprising a sheet of abrasive material connected to the base member and projecting from one side thereof.

* * * * *